United States Patent
Hadley et al.

(10) Patent No.: US 9,962,103 B2
(45) Date of Patent: May 8, 2018

(54) SYSTEMS AND METHODS FOR ASSESSING ELECTROCARDIOGRAM RELIABILITY

(71) Applicant: Cardiac Insight, Inc., Seattle, WA (US)

(72) Inventors: David M. Hadley, Woodinville, WA (US); Victor F. Froelicher, Jr., Menlo Park, CA (US)

(73) Assignee: Cardiac Insight, Inc., Kirkland, WA (US)

( * ) Notice: Subject to any disclaimer, the term of this patent is extended or adjusted under 35 U.S.C. 154(b) by 84 days.

(21) Appl. No.: 14/925,666

(22) Filed: Oct. 28, 2015

(65) Prior Publication Data
US 2016/0113541 A1   Apr. 28, 2016

Related U.S. Application Data

(60) Provisional application No. 62/069,777, filed on Oct. 28, 2014.

(51) Int. Cl.
*A61B 5/04* (2006.01)
*A61B 5/0468* (2006.01)
*A61B 5/0472* (2006.01)
*A61B 5/00* (2006.01)

(52) U.S. Cl.
CPC ........ *A61B 5/0468* (2013.01); *A61B 5/04012* (2013.01); *A61B 5/0472* (2013.01); *A61B 5/7203* (2013.01); *A61B 5/0006* (2013.01); *A61B 5/7207* (2013.01); *A61B 2503/10* (2013.01)

(58) Field of Classification Search
CPC ... A61B 5/0468; A61B 5/7203; A61B 5/0472; A61B 5/04012; A61B 2503/10; A61B 5/7207; A61B 5/0006
See application file for complete search history.

(56) References Cited

U.S. PATENT DOCUMENTS 5,634,468 A * 6/1997 Platt .................... A61B 5/0006
                                                128/903

* cited by examiner

*Primary Examiner* — Rex R Holmes
(74) *Attorney, Agent, or Firm* — Perkins Coie LLP

(57) ABSTRACT

The present technology is an automated method for determining whether a patient-specific electrocardiogram (ECG) is either (a) Normal and can be excluded from manual review or (b) Abnormal and included for manual review. In one embodiment, the method comprises comparing a plurality of characteristics of the ECG with predetermined subthreshold levels that are set less than clinically significant levels of abnormality of the characteristics, wherein the characteristics of the ECG are selected from the group including T-Wave inversion, ST-Depression, QT segment duration, delta wave character, anterior S-wave character and ectopic or pre-mature beats. The method continues by selecting the ECG for manual review if the plurality of selected characteristics exceed the predetermined subthreshold levels yet are below the corresponding clinically significant threshold levels of abnormality of the characteristics.

10 Claims, 8 Drawing Sheets

SYSTEMS AND METHODS FOR ASSESSING ELECTROCARDIOGRAM RELIABILITY

CROSS-REFERENCE TO RELATED APPLICATION(S)

This application claims the benefit of U.S. Provisional Application No. 62/069,777 filed Oct. 28, 2015, and incorporated herein by reference in its entirety.

TECHNICAL FIELD

The present technology relates generally to systems and methods for assessing electrocardiogram (ECG) reliability. In particular, several embodiments are directed to methods and associated systems for determining the accuracy of an automatically interpreted ECG.

BACKGROUND

Sudden cardiac arrest (SCA) in youth (e.g., less than 35 years of age) is an unfortunately common occurrence. Those participating in regular vigorous exercise are generally at higher risk for SCA. Additionally, risk of SCA has been shown to be stratified by gender (e.g., men have about 2× higher risk than women), ethnicity (e.g., African-Americans have about 2× higher risk than an overall population risk), and by sport (e.g., men's basketball athletes have about 4× higher risk than athletes in other sports). In a particular example, a men's collegiate basketball player (e.g., playing 4 years) has about a 1/800 chance of an SCA occurrence.

Recent studies have shown that for every 1,000 athletes screened by routine ECG, about 20-30 athletes have abnormal ECG's. Statistically, of the 20-30 abnormal ECG results, about 2-3 individual athletes will be found to have life-threatening conditions that need medical attention and/or intervention. Although many of these abnormalities will not result in sudden death, most of these conditions will be important in health management over the course of the individual athlete's life. Cardiovascular death is still the leading cause of death and disability in the United States and early detection of abnormal conditions is advantageous for treatment, management and SCA avoidance.

DETAILED DESCRIPTION

Figure 1:
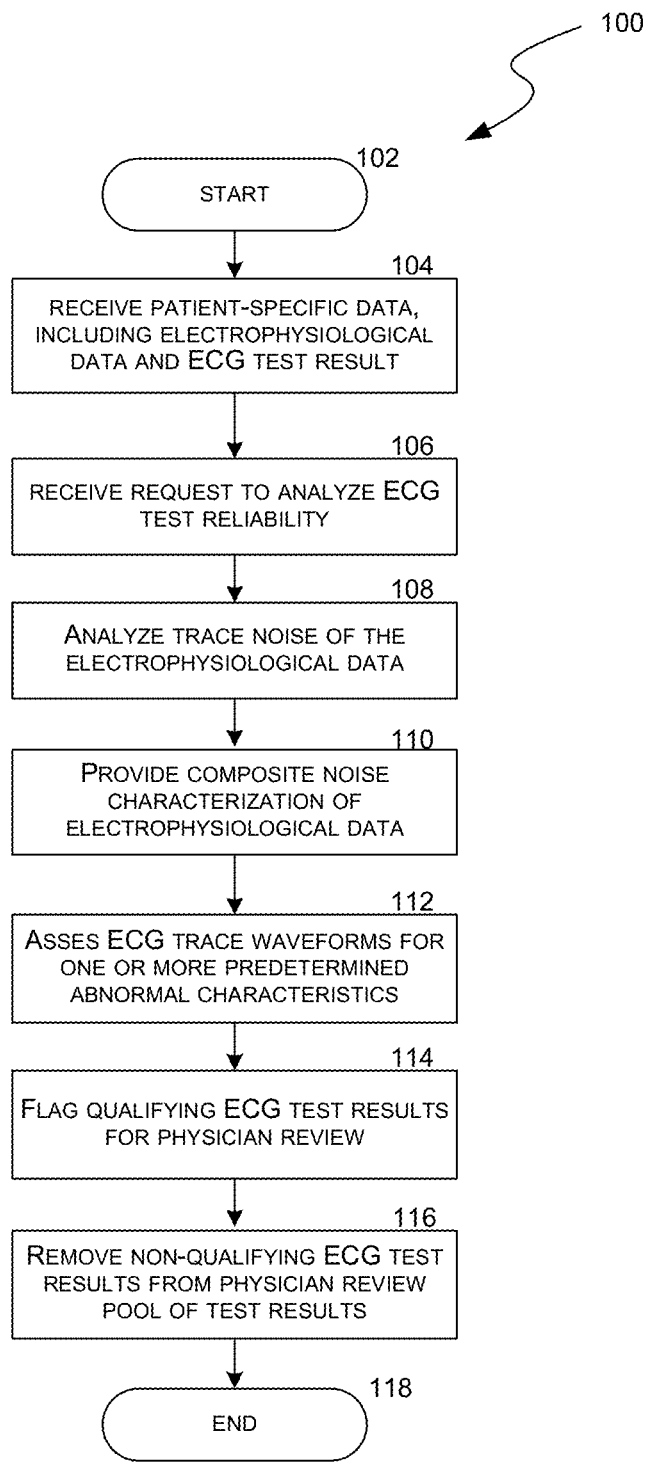
FIG. 1 is a flow diagram of a routine for assessing ECG machine diagnostic reliability in accordance with an embodiment of the present technology.

The following description provides specific details for a thorough understanding of, and enabling description for, embodiments of the technology. However, one skilled in the art will understand that the technology may be practiced without these details. In other instances, well-known components, applications, substitutes and functions have not been shown or described in detail to avoid unnecessarily obscuring the description of the embodiments of the disclosure.

The present disclosure is generally directed to methods and systems for assessing electrocardiogram (ECG) reliability. In particular, several embodiments are directed to methods and associated systems for determining the accuracy of an automatically interpreted ECG, such as determining the reliability of an automatically interpreted ECG Normal result. In various embodiments, the methods and systems disclosed herein can be provided for reducing the time and cost associated with physician review of automatically interpreted Normal ECG results.

Inclusion of an ECG exam in an athlete's Pre-Participation Exam (PPE) for athletic participation has been shown to greatly increase the detection of cardiovascular problems known to be associated with SCA. However, there has been substantial resistance in the United States to wide-scale inclusion of an ECG test during an athlete's PPE, primarily because of a high rate of false positive abnormality results and the cost of the ECG exam. A false positive ECG result can falsely indicate an athlete has a significant problem, which can result in large financial costs for additional diagnostic tests and can cause unnecessary psychological trauma to the athlete. False positives have been reduced through focused research efforts to develop appropriate ECG criteria for screening athletes. Historically, the false positive rate has been as high as 25%, and it is commonly acknowledged to average about 10%-15%. Through the use of improved ECG diagnostic criteria the false positive rate has dropped to about 3%. Continued research and diagnostic criteria development will likely lower this rate further.

Currently, the cost of a single ECG test is about US$25. Accordingly, wide-scale deployment of ECG testing of athletes could potentially significantly increase healthcare costs in the United States. A typical ECG test can be collected by an athletic trainer or medical technician, take about 5-8 minutes of total time, and require less than a dollar of material costs. The majority of the test cost is associated with physician time required to review the ECG. In many communities there can be an insufficient number of physicians with appropriate skill sets necessary for athlete ECG review, thus further restricting the potential use of the ECG in PPEs.

With the improvement in the ECG criteria, and the subsequent reduction in false positive rates, more than 95 percent of youth ECGs can be automatically diagnosed by the ECG device as Normal, i.e. no abnormal characteristics detected on the ECG. However, physicians continue to review all of the Normal records looking for the occasional machine interpretation error and associated false negatives.

In one embodiment, the present technology is directed to methods and systems that can identify ECGs that are automatically identified as "Normal" by an ECG machine but that include parameters and/or include characteristics that require physician review. Such embodiments are suitable for identifying "false negatives," and by extension, can identify ECG test results that are accurately interpreted as "Normal." In certain embodiments, physician review can be eliminated for "Normal" test results once potential "False Negative" results have been identified. By accurately identifying and filtering out the true Normal ECGs, physician review can be limited to ECG results showing irregularity or abnormality, thereby reducing cost and possibly improving physician accuracy and effectiveness.

Provided herein are routines and systems for assessing a reliability of automated and/or machine diagnostic test results from ECG tests. While some of the routines are described herein, one skilled in the art is capable of identifying other routines the system could perform. Moreover, the routines described herein can be altered in various ways. As examples, the order of illustrated logic may be rearranged, substeps may be performed in parallel, illustrated logic may be omitted, other logic may be included, etc.

FIG. 1 is a flow diagram of a routine 100 for assessing ECG machine diagnostic reliability in accordance with an embodiment of the present technology. The routine 100 can be invoked by a computing device, such as a client computer or mobile device, or in other embodiments, a server computer coupled to a computer network. In one embodiment the computing device includes an ECG diagnostic assessment application. As an example, the computing device may invoke the routine 100 after a client user engages a user computing device or other interface in communication with the computing device via a computer network.

The routine 100 begins at block 102 and a processor server receives patient-specific data (e.g., general patient information, patient identifier, electrophysiological data, ECG test results, etc.) (block 104). In some embodiments, the process server interprets the electrophysiological data using a digital processing system and clinically accepted criteria for abnormal physiological conditions; however, in other embodiments, the process server can receive the ECG test result (e.g., automated reading, diagnosis, etc.) from a separate server or from the ECG machinery. In these embodiments, a diagnostic assessment of the ECG results can be presented for physician review.

The process server receives a request to analyze the ECG test reliability (block 106) and analyzes the trace noise of the electrophysiological data (block 108). An aspect of the present technology is the identification that trace noise can contribute to diagnostic error through obscuring the onset and termination of cardiac phases, thus lowering the confidence in phase duration measurements. Further identified, noise may obscure details of the waveform such that important diagnostic characteristics are overlooked or incorrectly measured.

Figure 2:
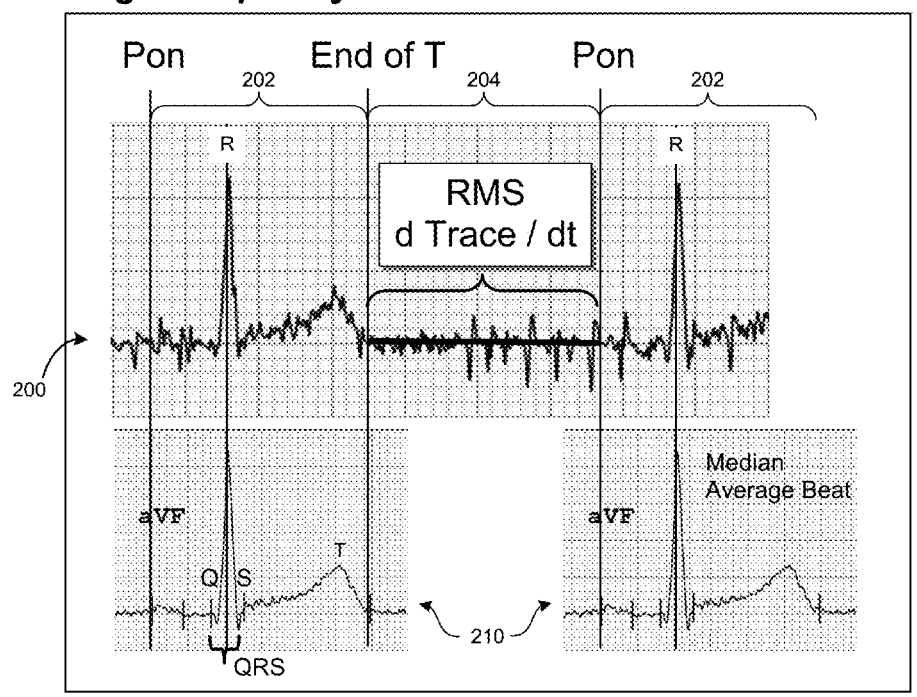
FIG. 2 is an ECG graph illustrating an example of high frequency noise in accordance with as aspect of the present technology.

In certain embodiments, trace noise can be divided into two general categories based upon the frequency content: high and low frequency noise. High frequency noise can be associated with poor electrode contact with the patient and patient muscle tremor, while low frequency noise can be associated with patient movement and breathing. For example, FIG. 2 is an ECG graph 200 illustrating an example of high frequency noise in accordance with as aspect of the present technology. The ECG graph 200 in FIG. 2 shows two cardiac cycles 202 that begin with the onset of atrial activation (Pon), followed by the peak of the ventricular depolarization (R), and continue through the ventricular repolarization cycle terminating at the end of the T-Wave portion (End of T). As illustrated in the ECG graph of FIG. 2, the heart pauses and then the cycle repeats.

One method for lowering noise is to time-align each cardiac cycle in the ECG record and average all of the beats to form a lower noise estimate of the ECG waveform. For example, FIG. 2 also shows two Median Average Beats 210 that are time aligned with the R waves. Although noise has been reduced in these average beats 210, the onsets of phases and waveform characteristics are still degraded by noise. The interval between the End of T for one cycle 202 and the Pon onset of the next cycle 202 provides a nominally quiet cardiac interval 204 for assessing inherent noise. In one embodiment, the step of analyzing the trace noise of the electrophysiological data (block 108) can use the root mean square (RMS) of the trace derivative to quantify the level of trace noise present in the interval. In another embodiment, the trace noise estimate can be derived using the RMS of the trace amplitude. And in a third embodiment, the trace noise can be quantified from the RMS trace amplitudes normalized by the R-wave peak amplitudes, which forms a signal to noise ratio. The analyzing step (block 108) can continue for all intervals in the individual ECG trace, and for all of the eight independent traces comprising the ECG record. In one embodiment, the highest value of the noise estimate can be selected as the high frequency quality metric for the record. In another embodiment, an average or median estimate can be derived from a plurality of the traces and can be used as the high frequency quality metric for the record.

Figure 3:
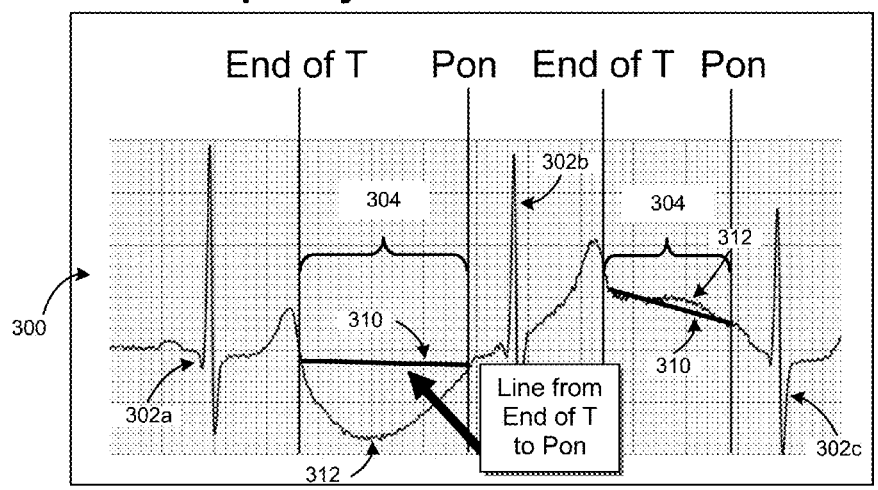
FIG. 3 is an ECG graph illustrating an example of low frequency noise in accordance with as aspect of the present technology.

FIG. 3 is an ECG graph 300 of several cycles 302 (identified individually as cycles 302a-c) illustrating an example of low frequency noise in accordance with as aspect of the present technology. As discussed above with respect to FIG. 2, a quiet cardiac interval 304 defined by the interval between the End of T of one cycle 310 and the Pon onset of the next cycle 310 can be identified in the ECG graph 300. The step of analyzing the trace noise of the electrophysiological data (block 108) can further include defining a line 310 from the End of T of one cycle (e.g., cycle 302a) to the Pon of the next cycle (e.g., cycle 302b). The RMS of the deviations of the trace 312 from the defined line 310 can provide an estimate of the long period trace noise. As discussed above with respect to high frequency noise, the interval with the largest RMS noise can be selected to characterize the ECG long period noise (e.g., low frequency noise; FIG. 3). In another embodiment, an average or median estimate can be derived from a plurality of the traces and can be used as the quality metric for the low frequency quality metric for the record.

The routine 100 can also include averaging together the high and low frequency noise estimates to provide a raw composite noise characterization of the ECG (block 110). In certain embodiments, the routine 100 averages each beat waveform together to form the average beat for measurement (e.g., the median average beats 210 in FIG. 2 compared with the raw trace in the upper part of FIG. 2). Increasing the number of beats averaged together can reduce the noise as the square root of the number of beats is included in the average. Since human heart rates vary from lows of 30 beats/min to highs well over 100 beats/minute, the raw noise estimate can be corrected or normalized by dividing by the square root of the number of beats included in the average. This normalized noise characterization can provide the basis for assessing the reliability of the ECG automated test result.

For example, the higher the normalized value, the more likely the automatic ECG interpretation may be in error. ECG's with a noise level above a predetermined threshold setting (e.g., approximately 15 µVolts) can also be designated as records requiring physician review or identified as defective ECGs. Likewise, ECG graphs (e.g., test results) that are automatically and/or machine-interpreted as "Normal" and which have noise levels below the predetermined threshold setting, can remain a candidate for exclusion from physician review. Thus, an optional aspect of the method is screening ECGs for noise so that only ECGs with noise below a predetermined threshold are eligible for being excluded from physician review using an automated process.

Figure 4:
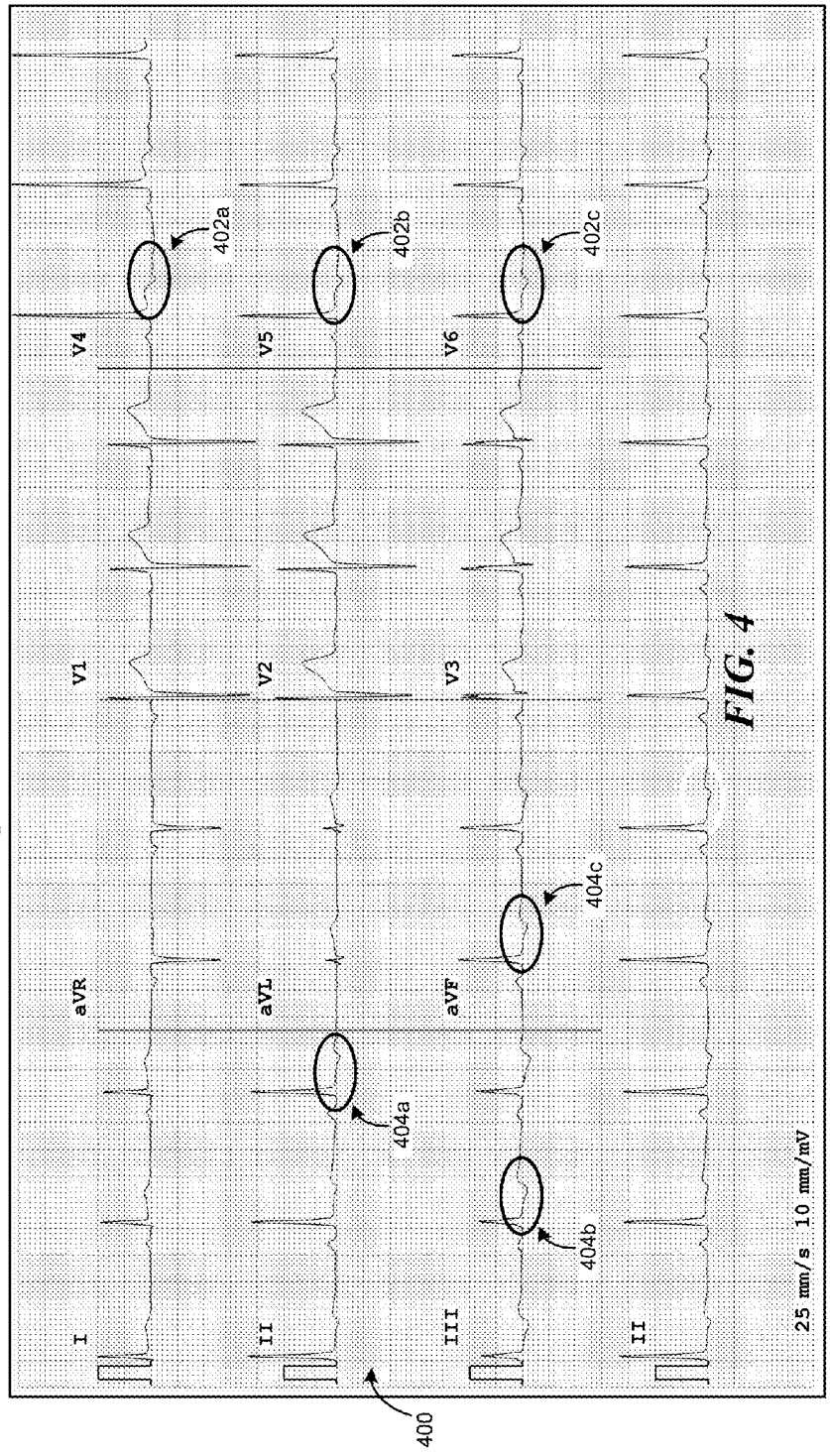
FIG. 4 is an ECG graph illustrating an example of electrophysiological data generated from a patient and in accordance with as aspect of the present technology.

Referring back to FIG. 1, and at block 112, one embodiment of the routine 100 can assess the ECG trace waveforms for a plurality (e.g., at least two) of predetermined subthreshold characteristics or parameters that categorize or flag the ECG for review by a physician, where "subthreshold" means that the characteristics or parameters are near, but not necessarily exceeding, accepted clinically significant threshold levels of abnormality. An alternative embodiment of the routine 100 can assess the same ECG characteristic of a plurality (e.g., at least two) ECG traces for at least one occurrence in the ECG traces of the characteristic exceeding a predetermined subthreshold level. In still another alternative embodiment, the routine can assess whether measured values of a single ECG characteristic in one or more ECG traces exceeds a subthreshold level, but not a higher accepted clinically significant threshold level of abnormality, and flag the data for physician review if this occurs in a plurality of occurrences. FIG. 4 is an ECG graph 400 illustrating an example of electrophysiological data generated from a patient and in accordance with as aspect of the present technology. In this example, the ECG graph shown in FIG. 4 is initially automatically and/or machine-identified as "Normal." However, the routine 100 can identify features of the ECG shown in FIG. 4 that meet one or more predetermined characteristics or parameters that flag the ECG graph for review by a physician. For example, the characteristics in the ECG graph of FIG. 4 include T-Wave (cardiac repolarization) inversions 402a-c in the lateral leads V4, V5 and V6, respectively, and T-Wave inversions 404a-d in the inferior leads II, III and aVF, respectively. As explained in more detail below, the characteristic can be identified by comparing the measured value of the T-Wave inversions to a subthreshold value for this characteristic. In several embodiments of the technology, the subthreshold value is selected to be less than the accepted clinically significant threshold value indicating an abnormality of the particular characteristic. Accordingly, the routine 100 of FIG. 1 is configured to identify and flag ECG test results for physician review that have previously been automatically and/or machine-identified to be "Normal" (e.g., using criteria used for automatically assessing the ECG).

Referring back to FIG. 1, the routine 100 continues by flagging ECG test results for physician review (block 114). If a patient's ECG data does not raise a flag (e.g., low noise characteristics and/or the ECG trace waveform characteristics do not exceed or otherwise meet the set threshold values of a plurality of the determined characteristics or parameters), the patient-specific data (e.g., the ECG data) may be removed from a physician review pool (block 116). The routine 100 may then continue at block 118, where it ends.

One aspect of the present technology is the recognition that the automatic criteria used to identify abnormal ECGs can also be leveraged to identify what would otherwise be noted as "Normal" records of concern for further physician review. In one embodiment, the subthreshold values of the characteristic that divide the identification of a "Normal" ECG from an "Abnormal" ECG can be selected to be lower or less than the conventional accepted clinically significant threshold levels of the characteristics indicating an abnormality. In some instances, automatic criteria are developed that balance Sensitivity and Specificity, with the goal of capturing patients with a particular condition (good Sensitivity), but not at the risk of overwhelming the physician with a large number of false positives (low Specificity). Medical best practice generally dictates that follow-up diagnostic tests are required when an ECG is declared abnormal. Accordingly, false positives are expensive and undesirable. Lowering the criteria to subthresholds of a plurality of the characteristics or a plurality of occurrences of a single characteristic in one or more ECG traces to increase Sensitivity (e.g., to near 100 percent), as provided by the present technology, can provide a robust method for automatically identifying records with concerning characteristics (e.g., predetermined characteristics and/or parameters) for physician review of the patient-specific data that conventional automated systems relying on full threshold values would otherwise identify as "Normal." Conversely, automated "Normal" records that continue to qualify as "Normal" following the routine 100 (FIG. 1), and thus have measured values of the characteristics that are less than selected lower "Abnormal" cutoff subthresholds continue to be identified as "Normal" and can forgo further physician review.

Particular individual ECG characteristics and subthresholds that can be used to divide truly "Normal" ECG results from ECG results flagged for physician review can include, for example, T-Wave inversion, ST-Depression, Long QT Syndrome, Wolff-Parkinson-White (WPW) syndrome, Arrhythmogenic Right Ventricular Dysplasia (ARVD), and Ectopic and Pre-Mature Beats. In one embodiment of the present technology, when the measured values of at least two of the individual ECG characteristics are below the selected lower "Abnormal" cutoff subthresholds, the patient-specific ECG can be flagged for physician review. For example, the patient-specific data is flagged for physician review when at least one occurrence of the measured values of the T-Wave inversion and ST-Depression exceed selected subthreshold values corresponding to each characteristic, and yet (b) the measured values for each characteristic do not exceed the accepted threshold values corresponding to the clinically significant findings of abnormality. In another embodiment of the present technology, when a plurality of the measured values of a single ECG characteristic exceed a subthreshold level but do not exceed a clinically accepted "Abnormal" threshold level, the patient specific data is flagged for physician review. Suitable ECG characteristics for this second embodiment include T-Wave inversion, ST-Depression, Long QT Syndrome, WPW, ARVD and Ectopic and Pre-Mature Beats. The present technology accordingly flags patient specific ECG data for physician review even though none of the measured values of the characteristics individually exceed the accepted threshold values corresponding to the clinically significant finding of abnormality. Further ECG characteristics and/or combinations of ECG characteristics can also be used and/or adjusted for improving detection and flagging of ECG results for physician review.

T-Wave Inversion.

The T-Wave reflects the repolarization, or recharging, of the ventricle. Normally the T-Wave is upright or positive, i.e. the waveform is above the baseline. For a T-Wave that peaks below the baseline, the accepted threshold value corresponding to a clinically significant finding of abnormality is an amplitude more negative than −100 µVolts. Thus, in conventional systems a T-Wave inversion that exceeds −100 µVolts is flagged as abnormal. In certain embodiments of the present technology, a lower subthreshold value can be set at −70 µVolts. With this reduced subthreshold, the plurality of T-Wave inversions 402*a-c* and 404*a-d* of the ECG 400 shown in FIG. 4 would cause the patient-specific data to be flagged for physician review even though they may not exceed −100 µVolts.

ST-Depression.

The accepted threshold value corresponding to a clinically significant finding of abnormality for ST-Depression is when the depression of the ST segment of the ECG is below the baseline by more than −50 µVolts. As demonstrated in FIG. 2, the median average beats 210, shows the QRS complex terminating in the end of the S-wave and the onset of the T-Wave. The junction between the end of S-wave and the beginning of the T-Wave is the ST segment, and a lower subthreshold value can, in one embodiment, be set at −30 µVolts. In one embodiment, when the ST-Depression exceeds −30 µVolts but is less than −50 µVolts for two or more ECG traces, the patient-specific data is flagged for physician review. In another embodiment, when a T-Wave depression is more than −70 µVolts but less than −100 µVolts and a ST-Depression is more than −30 µVolts but less than −50 µVolts, the patient-specific data is flagged for physician review.

Long QT Syndrome.

The QT segment is the duration of the section of ECG extending from the onset of the QRS complex to the End of T (see FIG. 2). The QT interval is a dynamic parameter and adjusts as heart rate increases or decreases. The QT parameter can be corrected to a standard heart rate of 60 beats/min, QTc, before assessing for an abnormal status. The accepted threshold value corresponding to a clinically significant finding of abnormality for Long QT Syndrome is a QTc greater than 500 msec. Records with large QT corrections associated with low heart rates (common in athletes) can also be flagged for review because the correction formula can be unreliable at low heart rates. In certain embodiments, QT or QTc greater than 460 msec, or QT corrections for heart rate greater than 25 msec, can define subthresholds for physician review.

WPW.

Figure 5:
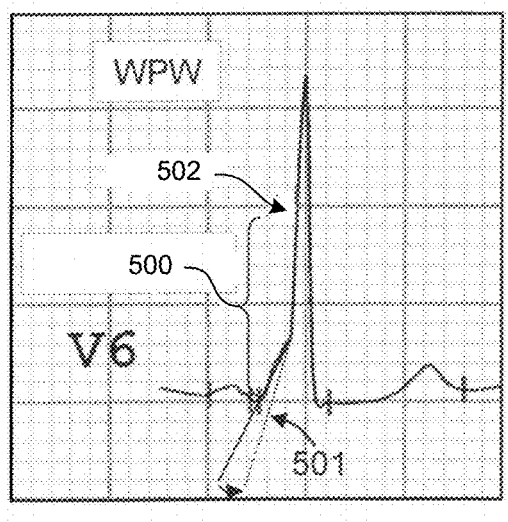
FIG. 5 is a portion of an ECG graph illustrating an example of assessing Wolff-Parkinson-White syndrome in accordance with an embodiment of the technology.

Wolff-Parkinson-White (WPW) syndrome reflects the presence of an auxiliary conductive pathway in the heart that can lead to a run-away ventricular heart rate (ventricular tachycardia) and SCA. The condition can be recognized on an ECG by a short time interval between the onset of the atrial contraction (Pon in FIG. 2) and the onset of the QRS complex, coupled with a distinctive shape of the front of the R wave (i.e. from the onset of the QRS complex to the Peak excursion), called a delta wave. Referring to FIG. 5, for example, a delta wave 500 has a marked change in slope between the early portion 501 of the wave (e.g., low slope) and the later portion 502 (e.g., high slope). In one embodiment, relaxing the delta wave change in slope criteria by 25% can define a subthreshold value for physician review.

ARVD.

Figure 6:
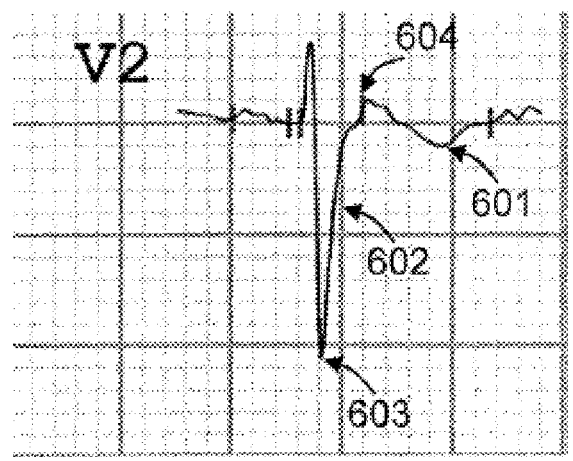
FIG. 6 is a portion of an ECG graph illustrating an example of assessing Arrhythmogenic Right Ventricular Dysplasia in accordance with an embodiment of the technology.

FIG. 6 is a graph of a portion of an ECG trace showing an example of Arrhythmogenic Right Ventricular Dysplasia characterized by a T-Wave inversion 601 in the anterior (V1-V3) leads and a concurrent slurring and delaying 604 of the S-wave 603 upstroke 602 in the same leads by more than 55 msec, as measured from the nadir of the S-wave to the end of the QRS. In one embodiment, delayed upstroke in the anterior leads greater than 55 msec, without T-Wave inversion, can define a threshold for physician review.

Ectopic and Pre-Mature Beats.

Figure 7:
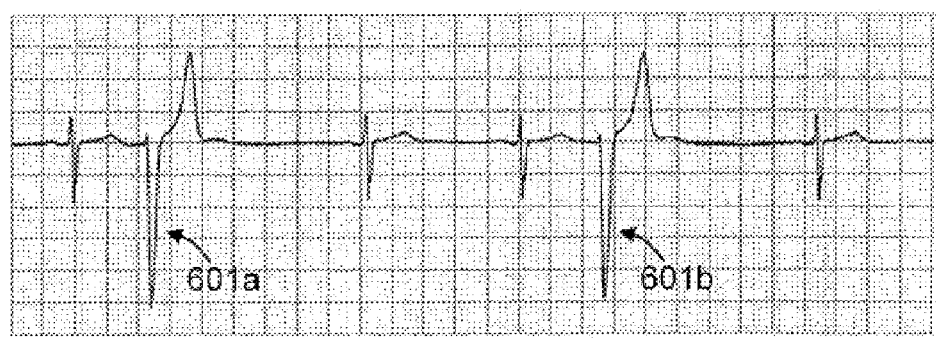
FIG. 7 is a portion of an ECG graph illustrating an example of assessing an ectopic heart beat in accordance with an embodiment of the technology.

Although an occasional ectopic or premature beat may be normal, in conventional analyses two or more of these type of beats within a standard 10 second duration of an ECG is considered abnormal. Relaxing the criteria to include a single ectopic or premature beat can be used, in one embodiment, to define a threshold for physician review. Referring to FIG. 7, for example, a single ectopic beat 601*a* or 601*b* within a predetermined period, such as a 10 second window, can be used to define the subthreshold level for physician review.

EXAMPLE 1

A method according to the present technology (e.g., the routine 100 of FIG. 1) was tested on a database of 5000+ ECG records collected from college athletes and reviewed by highly qualified sports cardiologists. Of the 5000 records, 167 records were identified as Abnormal by a conventional automatic interpretation system using conventionally accepted clinically significant threshold levels of abnormality and confirmed by the reviewing cardiologists. In this study, cardiologists had also identified an additional 22 records as requiring some degree of follow-up testing, even though the measured values of the separate characteristics of the records did not individually meet or exceed the specific abnormal threshold criteria corresponding to a clinically significant finding of abnormality used for conventional review. Following execution of the routine 100 (FIG. 1) all 22 of these records were correctly identified as needing further review. The routine determined that about 80% of the ECGs, (e.g., greater than 4000 patient records), did not require further physician review. Elimination of physician review of the truly "Normal" records would result in significant cost reduction without a loss in clinical efficacy.

EXAMPLE 2

Another aspect of the present technology combines noise analyses, conventional threshold level review, and one or more of the subthreshold level reviews explained above to determine "Normal" records that do not need additional manual review and "Abnormal" records that need manual review. For example, as a preliminary process the ECG record is removed from further processing and flagged for manual review when the trace noise level is determined to exceed a noise limit as set forth above, or the ECG record is further processed to determine if it is "Normal" or "Abnormal" if the trace noise level does not exceed the noise limit. The ECG record is then processed by assessing whether one or more characteristics or parameters of the ECG record exceed conventionally accepted threshold levels corresponding to clinically significant findings of abnormality. The ECG record is flagged as "Abnormal" and in need of manual review when one or more of the characteristics or parameters of the ECG record exceed the conventionally accepted threshold levels, or the record is identified as "Normal" when the ECG characteristics or parameters do not exceed the conventionally accepted threshold levels. The process continues by re-examining the "Normal" records identified by conventional processes. In this case, the "Normal" ECG record in which the characteristics or parameters do not exceed the conventionally accepted threshold levels is further processed by determining whether one or more of the characteristics or parameters exceed a subthreshold level. In the present technology, the ECG record is flagged as Abnormal and in need of manual review if at least one of the following occurs:
(1) at least one measured value of each of a plurality of different characteristics or parameters exceeds its sub-threshold level;
(2) at least two measured values of a single characteristic or parameter exceeds its subthreshold level.

One example of (1) above in which the ECG record is flagged as "Abnormal" and selected for manual review is when the T-Wave inversion value exceeds −70 µVolts and is less than −100 µVolts at least once, and the ST-Depression exceeds −30 µVolts and is less than −50 µVolts at least once. Examples of (2) above in which the ECG record is flagged as "Abnormal" and selected for manual review is when any one of the following occur two or more times in an ECG record: −70 µVolt T-Wave amplitude for T-Wave inversion; −30 µVolt ST segment depression value for ST-Depression; 460 msec duration of QT or QTc segment or QT correction greater than 25 msec for Long QT Syndrome; 20 percent reduced delta wave change in slope for WPW; 55 msec or larger delay of anterior S-wave upstroke for ARVD; or a single ectopic or pre-mature beat within a 10 second window.

Figure 8:
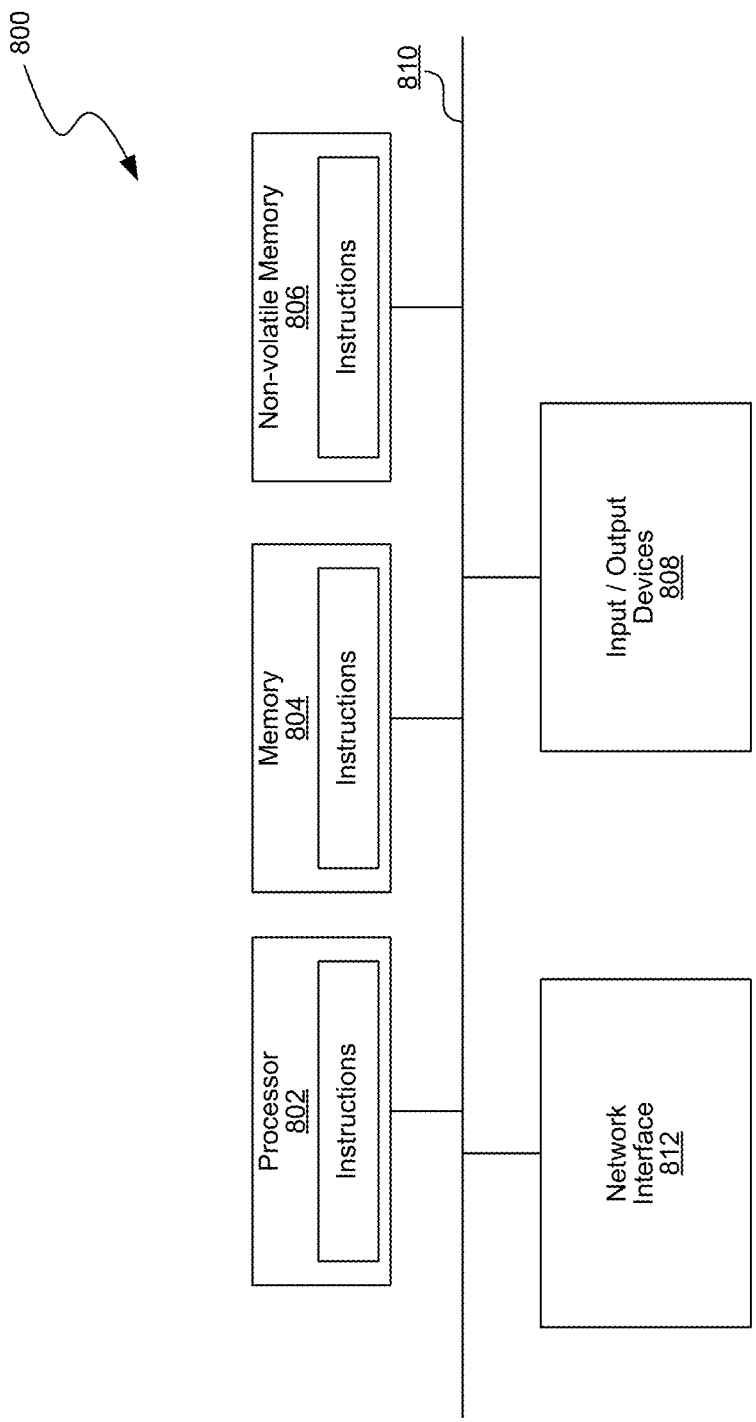
FIG. 8 is a diagrammatic representation of a machine in the example form of a computer system within which a set of instructions, for causing the machine to perform any one or more of the methodologies discussed herein, can be executed.

FIG. 8 shows a diagrammatic representation of a machine 800 in the example form of a computer system within which a set of instructions, for causing the machine to perform any one or more of the methodologies discussed herein, can be executed. In alternative embodiments, the machine 800 operates as a standalone device or can be connected (e.g., networked) to other machines. In a networked deployment, the machine can operate in the capacity of a server or a client machine in a client-server network environment, or as a peer machine in a peer-to-peer (or distributed) network environment.

The machine 800 can be a server computer, a client computer, a personal computer (PC), a mobile electronic user device, a tablet PC, a laptop computer, a set-top box (STB), a personal digital assistant (PDA), a cellular telephone or a smart phone (e.g., an iPhone or an Android phone), a web-enabled appliance, a network router, switch or bridge, a (hand-held) gaming device, a music player, or any machine capable of executing a set of instructions (sequential or otherwise) that specify actions to be taken by that machine.

The computing system 800 may include one or more central processing units ("processors") 802, main memory 804, non-volatile memory 806 (e.g., flash memory, hard disks, floppy disks, etc.), one or more input/output devices 808 (e.g., keyboard input devices, pointing devices, video display devices, etc.), and one or more network interface devices 812 for communication over a network 814, all of which are connected to an interconnect 810. The interconnect 810 is illustrated as an abstraction that represents any one or more separate physical buses, point to point connections, or both connected by appropriate bridges, adapters, or controllers. The interconnect 810, therefore, may include, for example, a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus, also called "Firewire."

The memory 804 and non-volatile memory 806 are computer-readable storage media that may store instructions that implement at least portions of the described technology. The instructions stored in memory 804 can be implemented as software and/or firmware to program the processor(s) 802 to carry out actions described above. In some embodiments, such software or firmware may be initially provided to the processing system 800 by downloading it from a remote system through the computing system 800 (e.g., via network interface 812).

While the machine-readable medium or machine-readable storage medium is shown in an exemplary embodiment to be a single medium, the term "machine-readable medium" and "machine-readable storage medium" should be taken to include a single medium or multiple media (e.g., a centralized or distributed database, and/or associated caches and servers) that store the one or more sets of instructions. The term "machine-readable medium" and "machine-readable storage medium" shall also be taken to include any medium that is capable of storing, encoding or carrying a set of instructions for execution by the machine and that cause the machine to perform any one or more of the methodologies of the presently disclosed technique and innovation.

In general, the routines executed to implement the embodiments of the disclosure, can be implemented as part of an operating system or a specific application, component, program, object, module or sequence of instructions referred to as "computer programs." The computer programs typically comprise one or more instructions set at various times in various memory and storage devices in a computer, and that, when read and executed by one or more processing units or processors in a computer, cause the computer to perform operations to execute elements involving the various aspects of the disclosure.

Moreover, while embodiments have been described in the context of fully functioning computers and computer systems, those skilled in the art will appreciate that the various embodiments are capable of being distributed as a program product in a variety of forms, and that the disclosure applies equally regardless of the particular type of machine or computer-readable media used to actually effect the distribution.

Further examples of machine-readable storage media, machine-readable media, or computer-readable (storage) media include, but are not limited to, recordable type media such as volatile and non-volatile memory devices, floppy and other removable disks, hard disk drives, optical disks (e.g., Compact Disk Read-Only Memory (CD ROMS), Digital Versatile Disks, (DVDs), etc.), among others, and transmission type media such as digital and analog communication links.

The network interface device 512 enables the machine to mediate data in a network with an entity that is external to the host server, through any known and/or convenient communications protocol supported by the host and the external entity. The network interface device 512 can include one or more of a network adaptor card, a wireless network interface card, a router, an access point, a wireless router, a switch, a multilayer switch, a protocol converter, a gateway, a bridge, bridge router, a hub, a digital media receiver, and/or a repeater.

The network interface device 512 can include a firewall which can, in some embodiments, govern and/or manage permission to access/proxy data in a computer network, and track varying levels of trust between different machines and/or applications. The firewall can be any number of modules having any combination of hardware and/or software components able to enforce a predetermined set of access rights between a particular set of machines and applications, machines and machines, and/or applications and applications, for example, to regulate the flow of traffic and resource sharing between these varying entities. The firewall can additionally manage and/or have access to an access control list which details permissions including for example, the access and operation rights of an object by an individual, a machine, and/or an application, and the circumstances under which the permission rights stand.

Other network security functions can be performed or included in the functions of the firewall, can be, for example, but are not limited to, intrusion-prevention, intrusion detection, next-generation firewall, personal firewall, etc. without deviating from the novel art of this disclosure.

Various embodiments of the technology are described above. It will be appreciated that details set forth above are provided to describe the embodiments in a manner sufficient to enable a person skilled in the relevant art to make and use the disclosed embodiments. Several of the details and advantages, however, may not be necessary to practice some embodiments. Additionally, some well-known structures or functions may not be shown or described in detail, so as to avoid unnecessarily obscuring the relevant description of the various embodiments. Although some embodiments may be within the scope of the claims, they may not be described in detail with respect to the Figures. Furthermore, features, structures, or characteristics of various embodiments may be combined in any suitable manner. Moreover, one skilled in the art will recognize that there are a number of other technologies that could be used to perform functions similar to those described above and so the claims should not be limited to the devices or routines described herein. While processes or blocks are presented in a given order, alternative embodiments may perform routines having steps, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times. The headings provided herein are for convenience only and do not interpret the scope or meaning of the claims.

The terminology used in the description is intended to be interpreted in its broadest reasonable manner, even though it is being used in conjunction with a detailed description of identified embodiments.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number, respectively. When the claims use the word "or" in reference to a list of two or more items, that word covers all of the following interpretations of the word: any of the items in the list, all of the items in the list, and any combination of the items in the list.

As used herein, a "module," an "interface," a "platform," or an "engine" includes a general purpose, dedicated or shared processor and, typically, firmware or software modules that are executed by the processor. Depending upon implementation-specific or other considerations, the module, interface, platform, or engine can be centralized or its functionality distributed. The module, interface, platform, or engine can include general or special purpose hardware, firmware, or software embodied in a computer-readable (storage) medium for execution by the processor.

Any patents, applications and other references, including any that may be listed in accompanying filing papers, are incorporated herein by reference. Aspects of the described technology can be modified, if necessary, to employ the systems, functions, and concepts of the various references described above to provide yet further embodiments.

These and other changes can be made in light of the above Detailed Description. While the above description details certain embodiments, no matter how detailed, various changes can be made. Implementation details may vary considerably, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the claims to the specific embodiments disclosed in the specification, unless the above Detailed Description section explicitly defines such terms. Accordingly, the actual scope of the claims encompasses not only the disclosed embodiments, but also all equivalents.

We claim:

1. An automated method for determining whether a patient-specific electrocardiogram (ECG) is either (a) Normal and can be excluded from manual review or (b) Abnormal and included for manual review, comprising:
   comparing a plurality of characteristics of the ECG with predetermined subthreshold levels that are set at less than clinically significant levels of abnormality for the characteristics, wherein the characteristics of the ECG are a T-Wave and an ST-Depression, and optionally include one or more ECG characteristics selected from the group consisting of QT segment duration, delta wave character, anterior S-wave character and ectopic or pre-mature beats; and
   selecting the ECG for manual review if the plurality of selected characteristics exceed the predetermined subthreshold levels are below the corresponding clinically significant threshold levels of abnormality of the characteristics.

2. The method of claim 1, wherein the subthreshold levels are −70 µVolt T-Wave amplitude, −30 µVolt ST segment depression value, 460 msec duration of QT or QTc segment or QT correction greater than 25 msec, a 20 percent reduced delta wave change in slope, 55 msec or larger delay of anterior S-wave upstroke, or occurrence of a single ectopic or pre-mature beat within a 10 second window.

3. The method of claim 2, wherein the clinically significant threshold levels of abnormality are −70 µVolts for T-Wave inversion and −30 µVolts for ST-Depression.

4. The method of claim 2 wherein the ECG is selected for manual review when T-Wave inversion value exceeds −70 µVolts and is less than −100 µVolts at least once, and ST-Depression exceeds −30 µVolts and is less than −50 µVolts at least once.

5. The method of claim 1 wherein, further comprising determining whether noise in the ECG is below a predetermined noise limit and either (i) excluding the ECG from further review if the noise is below the noise limit or (ii) accepting the ECG for further review if the noise is above the noise limit.

6. A system for automatically determining whether a patient-specific electrocardiogram (ECG) can be excluded from manual review or included for manual review, comprising:

a computer readable medium containing instructions the perform the following in a computer:

comparing a plurality of characteristics of the ECG with predetermined subthreshold levels that are set at less than clinically significant levels of abnormality for the characteristics, wherein the characteristics of the ECG are a T-Wave inversion and an ST-Depression, and optionally include one or more ECG characteristics selected from the group consisting of QT segment duration, delta wave character, anterior S-wave character and ectopic or pre-mature beats; and selecting the ECG for manual review if the plurality of selected characteristics exceed the predetermined subthreshold levels are below the corresponding clinically significant threshold levels of abnormality of the characteristics.

7. An automated method for determining whether a patient-specific electrocardiogram (ECG) is either (a) Normal and can be excluded from manual review or (b) Abnormal and included for manual review, comprising:

comparing at least two characteristics of the ECG with predetermined subthreshold levels that are set less than clinically significant levels of abnormality of the characteristics, wherein the characteristics of the ECG include a T-Wave inversion of −70 µVolts or an ST-Depression of −30 µVolts; and selecting the ECG for manual review if the selected characteristics exceed the predetermined subthreshold levels are below the corresponding clinically significant threshold levels of abnormality of the characteristics.

8. The method of claim 7 wherein the ECG characteristics further include one or more characteristics selected from the group including QT segment duration, delta wave character, anterior S-wave character and ectopic or pre-mature beats.

9. A system for automatically determining whether a patient-specific electrocardiogram (ECG) can be excluded from manual review or included for manual review, comprising:

a computer readable medium containing instructions the perform the following in a computer:

comparing at least two characteristics of the ECG with predetermined subthreshold levels that are set less than clinically significant levels of abnormality of the characteristics, wherein the characteristics of the ECG include a T-Wave inversion of −70 µVolts or an ST-Depression of −30 µVolts; and selecting the ECG for manual review if the selected characteristics exceed the predetermined subthreshold levels are below the corresponding clinically significant threshold levels of abnormality of the characteristics.

10. The system of claim 9 wherein the ECG characteristics further include one or more characteristics selected from the group including QT segment duration, delta wave character, anterior S-wave character and ectopic or pre-mature beats.

* * * * *